United States Patent [19]

Berg et al.

[11] Patent Number: 4,501,645

[45] Date of Patent: Feb. 26, 1985

[54] SEPARATION OF METHANOL FROM ACETONE BY EXTRACTIVE DISTILLATION

[76] Inventors: Lloyd Berg, 1314 S. Third Ave.; An-I Yeh, 709 S. 12th Ave., both of Bozeman, Mont. 59715

[21] Appl. No.: 547,654

[22] Filed: Nov. 1, 1983

[51] Int. Cl.³ .................. B01D 3/40; C07C 29/84; C07C 31/04; C07C 49/08

[52] U.S. Cl. ........................................ 203/51; 203/56; 203/57; 203/60; 203/62; 203/63; 568/411; 568/913

[58] Field of Search .................. 203/51, 62, 60, 63; 568/411, 913

[56] References Cited

U.S. PATENT DOCUMENTS

| | | | |
|---|---|---|---|
| 2,179,991 | 11/1939 | Bright et al. | 568/411 X |
| 2,617,757 | 11/1952 | Michael | 568/913 X |
| 3,031,384 | 4/1962 | Sirois et al. | 568/411 X |
| 3,073,752 | 1/1963 | Mention | 568/913 X |
| 3,419,477 | 12/1968 | Mattia | 568/411 X |

FOREIGN PATENT DOCUMENTS

| | | | |
|---|---|---|---|
| 911191 | 7/1946 | France | 203/51 |
| 156775 | 9/1982 | German Democratic Rep. | 203/51 |

*Primary Examiner*—Wilbur Bascomb

[57] ABSTRACT

Methanol cannot be completely removed from its mixture with acetone by distillation because of the presence of the minimum binary azeotrope. Methanol can be readily removed from mixtures containing it and acetone by using extractive distillation to bring off the methanol as overhead product in a rectification column by using extractive distillation in which the extractive distillation agent is an effective higher boiling organic compound or a mixture of these. Typical examples of effective agents are acetophenone, 3-pentanone, 2,4-pentanedione, ethylacetoacetate, 2-butanone plus benzil.

9 Claims, No Drawings

SEPARATION OF METHANOL FROM ACETONE BY EXTRACTIVE DISTILLATION

FIELD OF THE INVENTION

This invention relates to a method for separating methanol from acetone using certain higher boiling liquids as the extractive agent in extractive distillation.

DESCRIPTION OF PRIOR ART

Extractive distillation is the method of separating close boiling compounds of azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus either require fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these components are the use of another rectification column, cooling and phase separation, or solvent extraction.

Acetone and methanol are two of the most widely used solvents and mixtures of these two occur with great frequency. The usual method of recovering volatile solvents is by rectification in multiplate column. However in this case, complete recovery by rectification is impossible due to the formation of the minimum azeotrope between these two. Acetone, b.p. 56.1° C. and methanol, b.p. 64.5° C. form a minimum azeotrope boiling at 55.7° C. at one atmosphere pressure and containing 88 weight percent acetone, 12 weight percent methanol. As pressure is increased, the azeotrope composition gets richer in methanol, thus 34% at 4.56 Atm., 46% at 7.82 Atm. and 56% at 11.6 Atm. It is therefore impossible to produce pure methanol from acetone-methanol mixtures by rectification because the lower boiling azeotrope will always come off overhead as the initial product. Any mixture of acetone and methanol subjected to rectification at one atmosphere pressure will produce an overhead product boiling at 55.7° C. and containing 88% acetone, 12% methanol. Extractive distillation would be an attractive method of effecting the separation of methanol from acetone if agents can be found that (1) will break the acetone-methanol azeotrope and (2) are easy to recover from the acetone, that is form no azeotrope with acetone and boil sufficiently above acetone to make the separation by rectification possible with only a few theoretical plates.

Extractive distillation typically requires the addition of an equal amount to twice as much extractive agent as the acetone-methanol on each plate in the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery in the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with acetone otherwise it will form a two phase azeotrope with the acetone in the recovery column and some other method of separation will have to be employed.

The breaking of this azeotrope by extractive distillation is new. Applications of this concept might be the breaking of the ethanol-water azeotrope. J. Schneible, U.S. Pat. No. 1,469,447 used glycerol, P. V. Smith and C. S. Carlson, U.S. Pat. No. 2,559,519 employed ethoxy-ethanol and butoxyethanol for this purpose and W. E. Catterall, U.S. Pat. No. 2,591,672 reported gasoline as being effective. These are dehydrations and operate more conventionally as a solvent extraction process rather than an extraction distillation. The closest application of this concept is probably L. Berg and P. Ratanapupech, U.S. Pat. No. 4,379,028 "The Separation of Ethylacetate from Ethanol and Water by Extractive Distillation".

OBJECTIVE OF THE INVENTION

The object of this invention is to provide a process or method of extractive distillation that will enhance the relative volatility of methanol from acetone in their separation in a rectification column. It is a further object of this invention to identify suitable extractive distillation agents which will eliminate the acetone-methanol binary azeotrope and make possible the production of pure methanol and acetone by rectification. It is a further object of this invention to identify organic compounds which, in addition to the above constraints, are stable, can be separated from acetone by rectification with relatively few theoretical plates and can be recycled to the extractive distillation column and reused with little decomposition.

SUMMARY OF THE INVENTION

The objects of this invention are provided by a process for separating methanol from acetone which entails the use of certain oxygenated or chloro organic compounds as the agent in extractive distillation.

DETAILED ELABORATION OF THE INVENTION

We have discovered that certain oxygenated and/or chloro organic compounds, both singly and in mixtures, will effectively negate the acetone-methanol minimum azeotrope and permit the separation of pure methanol from acetone by rectification when employed as the agent in extractive distillation. In a companion application Ser. No. 06/393,071, June 6, 1982, is described the separation of acetone from methanol by extractive distillation in which the acetone is removed as the overhead product. Since acetone normally boils lower than methanol, this is the expected result. We have discovered that there are certain compounds and their mixtures which when employed as extractive distillation agents, will remove the methanol as the overhead product.

Table 1 lists the compounds, mixtures and approximate proportions that we have found to be effective. The data in Table 1 was obtained in a vapor-liquid equilibrium still. In each case, the starting material was the acetone-methanol azeotrope. The ratios are the parts of extractive agent used per part of acetone-methanol azeotrope.

The compounds that are effective as extractive distillation agents when used alone are methyl ethyl ketone, pentanone-2, pentanone-3, heptanone-2, heptanone-3, methyl isobutyl ketone, methyl isoamyl ketone, acetophenone, 2,4-pentanedione, acetonyl acetone, methyl acetoacetate, ethyl acetoacetate, octanone-2, diacetone alcohol, cyclopentanone, cyclohexanone, undecanone-2, chloro-2-propanone, 2,5-hexanedione, diisobutyl ketone, 4-methyoxy-4-methyl pentanone-2, phenyl ethyl ketone, phorene, 3-hexen-2-one, o-hydroxyacetophenone. The compounds which are effective when used as mixtures are acetophenone, benzophenone, ethylacetoacetate, p-hydroxyacetophenone, fluorenone, 4-hydroxy-4-methoxybenzophenone, 3-hexen-2-one, m-hydroxyacetophenone, m-nitroacetophenone.

TABLE 1

Extractive Distillation Agents Which are Effective In Separating Methanol From Acetone.

| Compounds | Ratio | Relative Volatility |
|---|---|---|
| Methyl ethyl ketone | 5/3 | 1.35 |
| 3-Pentanone | 4/3 | 1.41 |
| 2-Pentanone | 4/3 | 1.32 |
| 3-Heptanone | 4/3 | 1.82 |
| Methyl isobutyl ketone | 4/3 | 1.49 |
| Methyl isoamyl ketone | 4/3 | 1.39 |
| Acetophenone | 5/3 | 2.27 |
| Methyl ethyl ketone, Benzil | 1.5:1 | 1.68 |
| 2,4-Pentanedione | 5/3 | 1.89 |
| Acetonylacetone | 5/3 | 1.67 |
| Methylacetoacetate | 5/3 | 1.47 |
| Ethylacetoacetate | 5/3 | 2.17 |
| 2-Heptanone | 2 | 1.39 |
| 2-Octanone | 2 | 1.79 |
| Diacetone alcohol | 2 | 1.02 |
| Cyclopentanone | 2 | 1.41 |
| Cyclohexanone | 2 | 1.28 |
| 2-Undecanone | 2 | 1.49 |
| Chloro-2-propanone | 2 | 1.64 |
| 2,5-Hexanedione | 2 | 1.20 |

TABLE 1-continued

Extractive Distillation Agents Which are Effective In Separating Methanol From Acetone.

| Compounds | Ratio | Relative Volatility |
|---|---|---|
| 4-Hydroxyacetophenone, Ethylacetoacetate | 1:1 | 1.30 |
| Benzophenone, Acetophenone | 1:1 | 1.79 |
| Diisobutyl ketone | 2 | 1.37 |
| 4-Methoxy-4-methylpentanone-2 | 2 | 1.33 |
| Phenyl ethyl ketone | 2 | 1.47 |
| Fluorenone, Acetophenone | 1:1 | 1.67 |
| 4-Hydroxy-4-methoxybenzophenone, Acetophenone | 1:1 | 1.67 |
| Ethyl butyl ketone | 2 | 1.79 |
| Diacetyl, Acetophenone | 1:1 | 1.35 |
| Phorone | 2 | 1.41 |
| 3-Hexen-2-one | 4/3 | 3.03 |
| 3-Hexen-2-one, Acetophenone | 4/3:2/3 | 1.61 |
| o-Hydroxyacetophenone | 2 | 1.89 |
| m-Hydroxyacetophenone, Acetophenone | 1:1 | 1.12 |
| m-Nitroacetophenone, Acetophenone | 1:1 | 1.44 |

Several of the compounds and mixtures listed in Table 1 and whose relative volatility had been determined in the vapor-liquid equilibrium still, were then evaluated in a glass perforated plate rectification column possessing 4.5 theoretical plates. The results are listed in Table 2. The methanol-acetone azeotrope contains 12 weight percent methanol, 88 weight percent acetone and in every case in Table 2. The "blank" run was made to demonstrate the normal procedure in a rectification column. The overhead product, 10 wt.% methanol, approaches the azeotrope which is 12% methanol. The remainder of the runs are with appropriate extractive distillation agents. Before extractive distillation agent is pumped in, the overhead approaches the azeotrope and the temperature is 53.6° C. When extractive distillation agent is added, the overhead temperature rises as methanol replaces the azeotrope as the overhead product and the overhead temperature is in the range of 57°–72° C. depending on which agent is used. As the run proceeds, the extractive distillation agent accumulates in the stillpot and so the stillpot temperature rises to that corresponding to the mixture present in it.

Frequently the stillpot temperature is lower than the overhead temperature. For example, with methyl ethyl ketone, after two hours, the stillpot temperature was 68.8° C. and the overhead temperature was 70.4° C.

Table 3 shows the results of using four different methanol-acetone concentrations with methyl ethyl ketone as the extractive distillation agent in the 4.5 theoretical plate glass perforated plate column. In every case, the azeotrope is negated and the overhead is richer in methanol than the stillpot or bottoms composition. This shows that the extractive distillation agent is effective over the entire range of concentration.

TABLE 2

| | Data From Runs Made In Rectification Column | | | | | |
|---|---|---|---|---|---|---|
| | Overhead | Stillpot Temp., °C. | | Wt. % of Methanol | | Relative |
| Compounds | Temp., °C. | At start | After 2 hrs | Overhead | Bottoms | Volatility |
| Blank | 50.2 | 53.8 | 53.6 | 10.0 | 7.0 | 1.09 |
| Methyl ethyl ketone | 70.4 | 55.6 | 68.8 | 31.1 | 6.2 | 1.53 |
| 2-Pentanone | 72 | 55 | 78 | 43.6 | 7.3 | 1.66 |
| 3-Pentanone | 70 | 55 | 77 | 43.9 | 5.8 | 1.76 |
| Methyl isobutyl ketone | 69.2 | 53.2 | 77.8 | 24.7 | 5.3 | 1.48 |
| Methyl isoamyl ketone | 67.2 | 54.8 | 83.0 | 30.9 | 4.6 | 1.64 |
| 2,4-Pentanedione | 65 | 56 | 93 | 51.6 | 5.5 | 1.91 |
| Diisobutyl ketone | 61.4 | 54.6 | 79.6 | 31.8 | 4.8 | 1.64 |
| Acetophenone | 57 | 55.2 | 91.4 | 38.3 | 5.3 | 1.71 |
| Ethyl acetoacetate | 58 | 54 | 95 | 34.8 | 5.9 | 1.77 |

TABLE 2-continued

| | Data From Runs Made In Rectification Column | | | | | |
|---|---|---|---|---|---|---|
| | Overhead | Stillpot Temp., °C. | | Wt. % of Methanol | | Relative |
| Compounds | Temp., °C. | At start | After 2 hrs | Overhead | Bottoms | Volatility |
| Methyl ethyl ketone + Benzil* | 67 | 55 | 74 | 43.2 | 6.8 | 1.68 |

Notes:
Mixture used comprised 7 wt. % methanol, 93 wt. % acetone
Addition conditions: Extr. distn. agents added at 20 ml/min. & 25° C.
Total reflux rate: 10–16 ml/min.
*Wt. ratio of methyl ethyl ketone to benzil is 1.5:1.

TABLE 3

Products Obtained From Different Feed Composition Using Methyl ethyl ketone As The Extractive Distillation Agent.

| Feed Composition Wt. % of Methanol | Overhead Composition Wt. % of Methanol | Bottoms Composition Wt. % of Methanol | Relative Volatility |
|---|---|---|---|
| 7 | 31.1 | 6.2 | 1.53 |
| 25 | 72.4 | 29.2 | 1.51 |
| 55 | 84.5 | 64.7 | 1.27 |
| 80 | 97.6 | 94.4 | 1.21 |

THE USEFULNESS OF THE INVENTION

The usefulness or utility of this invention can be demonstrated by referring to the data presented in Tables 1, 2 and 3. All of the successful extractive distillation agents show that methanol can be removed from its binary minimum azeotrope with acetone by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity methanol from any mixture with acetone including the minimum azeotrope. The stability of the compounds used and the boiling point difference is such that complete recovery and recycle is obtainable by a simple distillation and the amount required for make-up is small.

WORKING EXAMPLES

Example 1

The methanol-acetone azeotrope is 12 weight percent methanol, 88 weight percent acetone. Thirty grams of the methanol-acetone azeotrope and 25 grams of ethyl acetoacetate were charged to an Othmer type glass vapor-liquid equilibrium still and refluxed for six hours. Analysis of the vapor and liquid by gas chromatography gave vapor 90.4% acetone, 9.6% methanol; liquid of 95.3% acetone, 4.7% methanol. This indicates a relative volatility of 2.17.

Example 2

Thirty grams of methanol-acetone azeotrope, 15 grams of fluorenone and 15 grams of acetophenone were charged to the vapor-liquid equilibrium still and refluxed for seven hours. Analysis indicated a vapor composition of 83.1% acetone, 16.9% methanol, a liquid composition of 89.2% acetone, 10.8% methanol which is a relative volatility of 1.67.

Example 3

A glass perforated plate rectification column was calibrated with ethylbenzene and p-xylene which possesses a relative volatility of 1.06 and found to have 4.5 theoretical plates. A solution of 35 grams of methanol and 465 grams of acetone was placed in the stillpot and heated. When refluxing began, an extractive agent consisting of 2,4-pentanedione was pumped into the column at a rate of 20 ml/min. The temperature of the extractive agent as it entered the column was 25° C. After establishing the feed rate of the extractive agent, the temperature of the methanol and acetone in the stillpot was adjusted to give a total reflux rate of 10–20 ml/min. After one hour of operation, overhead and bottoms samples of approximately two ml. were collected and analysed by gas chromatography. The overhead analysis was 46.8% acetone, 53.2% methanol. The bottoms analysis was 93.5% acetone and 6.5% methanol. Using these compositions in the Fenske equation, with the number of theoretical plates in the column being 4.5, gave an average relative volatility of 1.86 for each theoretical plate. After 1.5 hours of total operating time, the overhead and bottoms samples were again taken and analysed. The overhead composition was 48.4% acetone, 51.6% methanol and the bottoms composition was 94.5% acetone and 5.5% methanol. This gave an average relative volatility of 1.91 for each theoretical plate. After two hours of total operating time, the overhead and bottoms samples were again taken and analysed. The overhead composition was 48.4% acetone, 51.6% methanol and the bottoms composition was 96.2% acetone, 4.8% methanol. This gave an average relative volatility of 1.97 for each theoretical plate.

Example 4

A solution of 35 grams of methanol and 465 grams of acetone was placed in the stillpot of the same column used in Example 3 and heat applied. When refluxing began an extractive agent consisting of 60% methyl ethyl ketone and 40% benzil was fed into the top of the column at a feed rate of 20 ml/min. and a temperature of 25° C. After establishing the feed rate of the extractive agent, the temperature of the acetone and methanol in the stillpot was adjusted to give a total reflux rate of 10–20 ml/min. Having established the reflux rate, the column was allowed to operate for one hour. After one hour of steady operation, overhead and bottoms samples of approximately two ml. were collected and analysed using gas chromatography. The overhead analysis was 56.8% acetone, 43.2% methanol. The bottoms analysis was 93.2% acetone and 6.8% methanol. Using these compositions in the Fenske equation with the number of theoretical plates of the column being 4.5, gave an average relative volatility of 1.68 for each theoretical plate. After 1.5 hours of total operation, the overhead composition was 62.4% acetone and 37.6% methanol and the bottoms composition was 93.2% acetone, 6.8% methanol. This gave an average relative volatility of 1.60 for each theoretical plate. After two hours of total operation, the overhead composition was 64% acetone, 36% methanol and the bottoms composition was 95.3% acetone, 4.7% methanol. This gave an average relative volatility of 1.72 for each theoretical plate.

We have shown that by the use of the proper compound or combination of compounds as agents, methanol can be effectively removed from its mixture with acetone in any proportion including the minimum azeotrope.

The nature of the present invention having been described, what we wish to claim as new and useful and secure by Letters Patent is:

1. A method for recovering essentially pure methanol from a mixture of methanol and acetone which comprises distilling a mixture of methanol and acetone in a rectification column in the presence of an effective amount of an extractive agent, recovering essentially pure methanol as overhead and obtaining the extractive agent plus acetone from the stillpot or reboiler, the extractive agent is one or more aliphatic ketones containing from four to eleven carbon atoms.

2. The method of claim 1 in which the extractive agent consists of one or more of 2-butanone, 2-pentanone, 3-pentanone, 3-heptanone, methyl isobutyl ketone, methyl isoamyl ketone, 2,4-pentanedione, acetonylacetone, 2-heptanone, 2-octanone, diacetone, cyclopentanone, cyclohexanone, 2-undecanone, chloro-2-propanone, diisobutyl ketone, ethyl butyl ketone, diacetyl, phorone, methylacetoacetate, ethylacetoacetate, 2,5-hexanedione, 4-methoxy-4-methylpentanone-2, or 3-hexen-2-one.

3. A method for recovering essentially pure methanol from a mixture of methanol and acetone which comprises distilling a mixture of methanol and acetone in a rectification column in the presence of an effective amount of an extractive agent, recovering essentially pure methanol as overhead and obtaining the extractive agent plus acetone from the stillpot or reboiler, the extractive agent is one or more aromatic ketones containing from eight to fourteen carbon atoms.

4. The method of claim 3 in which the extractive agent consists of one or more of acetophenone, benzil, 4-hydroxyacetophenone, benzophenone, phenyl ethyl ketone, fluorenone 4-hydroxy-4-methoxybenzophenone, o-hydroxyacetophenone, m-hydroxyacetophenone, or m-nitroacetophenone.

5. A method for recovering essentially pure methanol from a mixture of methanol and acetone which comprises distilling a mixture of methanol and acetone in a rectification column in the presence of an effective amount of an extractive agent, recovering essentially pure methanol as overhead and obtaining the extractive agent plus acetone from the stillpot or reboiler, the extractive agent includes a mixture of at least one aliphatic ketone containing from four to eleven carbon atoms and at least one aromatic ketone containing from eigth to fourteen carbon atoms.

6. The method of claim 5 in which the extractive agent consists of a mixture of 2-butanone and benzil.

7. The method of claim 5 in which the extractive agent consists of a mixture of ethylacetoacetate and 4-hydroxyacetophenone.

8. The method of claim 5 in which the extractive agent consists of a mixture of diacetyl and acetophenone.

9. The method of claim 5 in which the extractive agent consists of a mixture of 3-hexen-2-one and acetophenone.

* * * * *